United States Patent [19]

Horn

[11] Patent Number: 4,619,256
[45] Date of Patent: Oct. 28, 1986

[54] INTRAOCULAR LENS INSERTING ASSEMBLY

[76] Inventor: Gerald Horn, 5415 W. Sheridan Rd., Chicago, Ill. 60640

[21] Appl. No.: 415,806

[22] Filed: Sep. 8, 1982

[51] Int. Cl.⁴ .......................... A61B 17/00; A61F 2/16
[52] U.S. Cl. ..................................... 128/303 R; 623/6
[58] Field of Search .............. 3/13; 128/303 R; 623/6

[56] References Cited

U.S. PATENT DOCUMENTS

| | | | |
|---|---|---|---|
| 4,136,406 | 1/1979 | Norris | 3/13 |
| 4,251,887 | 2/1981 | Anis | 3/13 |
| 4,349,027 | 9/1982 | DiFrancesco | 128/303 R |

*Primary Examiner*—Ronald L. Frinks
*Attorney, Agent, or Firm*—Kane, Dalsimer, Kane, Sullivan and Kurucz

[57] ABSTRACT

An assembly for inserting an intraocular lens into an eye having an elongated first member with two side walls for closing the haptics of lens around the lens and a second member between said walls. The lens is placed on the second member with the haptics being engaged by the walls of the first member. The part of the assembly holding the lens is introduced into the eye and then the lens is released by withdrawing the first member and thus disengaging the haptics.

4 Claims, 8 Drawing Figures

U.S. Patent     Oct. 28, 1986     4,619,256
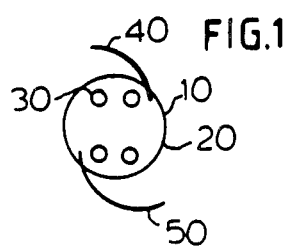
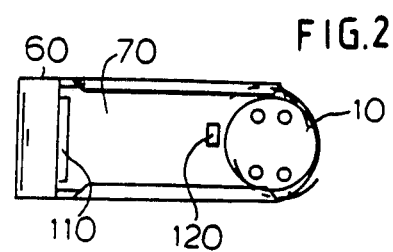
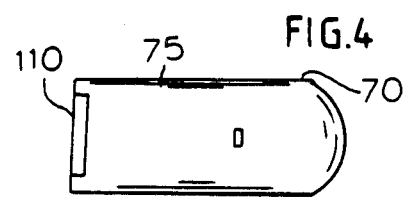
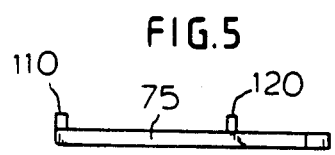
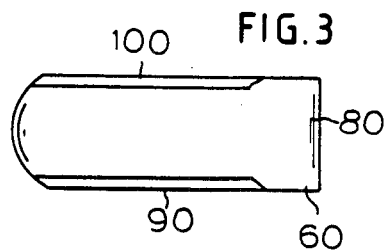
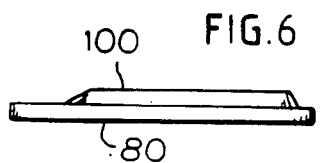
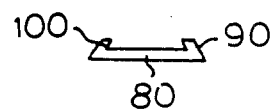
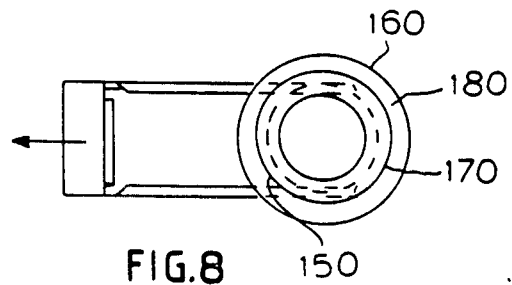

INTRAOCULAR LENS INSERTING ASSEMBLY

BACKGROUND OF THE INVENTION

This invention pertains to a tool for inserting an intraocular lens into the eye.

Various diseases of the human eye may require removal of the eye's natural lens. For example, one of these diseases causes the natural lens to become opaque, thus blocking the light before it hits the retina. This effect is commonly referred to as a cataract.

After the lens has been removed, an artificial lens must be provided to restore the patient's vision. Generally, there are three methods of providing such lens: regular glasses, external contact lens and intraocular lens.

Regular glasses used for cataracts are very thick and therefore found aesthetically objectionable by many patients. Contact lenses are inappropriate to some patients, especially older ones who do not have the dexterity necessary for inserting or removing the lenses. Thus, for many patients the intraocular lens present the best alternative.

Depending on their actual position within the eye, intraocular lenses are categorized either as anterior chamber lenses or posterior chamber lenses. As the name implies an anterior chamber lens is installed in the anterior chamber between the iris and the ocular jelly. Sometimes, this lens is positioned in the plane of the iris. In order to insure that the lens does not shift, the lens is sometimes sutured or otherwise affixed to the iris. Anterior chamber lenses are the predominant and safer type of lenses, and, of course, they must be used after intracapsular surgery during which the capsular bag is removed.

Posterior chamber lenses can be used after extracapsular surgery, i.e., when the cataract is removed but the capsular bag is left in place. Although posterior chamber lenses may be positioned between the bag and the iris, it was found that it is safer to install these lenses within the capsular bag itself.

Intraocular lenses have gone through an evolution of their own. While the initial lenses had bulky, complicated appendages for securing the lens within the eye, the latest lenses have much simpler mechanisms. One of the most common types of intraocular lens has a number of flexible loops or haptics. In the relaxed position, these loops are coplanar with the lens and engage the side walls of the eye in a spring action, thus holding the lens in place. The loops are made of polypropylene or other similar material and lenses are available with loops of a variety of sizes, shapes and colors.

It is well known that eye surgery is a very delicate procedure. Any inadvertent move on the part of the surgeon may further damage the eye. This is especially true for the process of implanting an intraocular eye because the lens itself is very small and, further, it must be precisely positioned so that it can focus the light entering the eye onto the retina. The lenses with loops are especially difficult to install because the loops in their open position cover an area which is much larger than the actual area of the lens. Various devices have been made which assist the surgeon in this procedure, however most of them are too bulky and expensive.

One device which has been used in particular with lenses having loops is the so-called SHEET GLIDE. This device is simply a flat flexible plastic strip which is slightly narrower than the diameter of the lens. In order to use this device, the surgeon makes an appropriate incision in the eye, and then slips the SHEET GLIDE into the eye with its tip positioned in the general location to be occupied by the lens. Next, he slides the lens on the glide into the eye. The incision in the eye must be large enough to accommodate the loops, and the SHEET GLIDE does not provide any protection of the eye during the implantation.

OBJECTIVES AND SUMMARY OF THE INVENTION

Therefore, it is the objective of this invention to provide a tool for inserting an intraocular lens in the eye which protects the eye during insertion.

Another objective is to provide a tool which requires a smaller opening then previously disclosed, thus making the operation safer.

A further objective is to provide a tool which keeps the loops close to the lens while the lens is being positioned within the eye.

Other objectives and advantages of the invention shall be described in the following description.

In accordance with the invention, there is provided an assembly for inserting an intraocular lens with loops or haptics into an eye, said assembly comprising a first and a second member. The first member has a flat, elongated portion and has two opposing walls extending at least partially along said portion. The second member is also flat and it is slidably inserted between the two walls of the first member. The two members cooperate in a manner so that when a lens is placed on the second member, the haptics of the lens engage the two walls, thus holding the lens secure.

After a suitable opening is made in the eye, the assembly is introduced partially into the eye until the lens is in the desired position. Then the first member is separated from the assembly by retracting it from the eye while the second member is held in position. This motion allows the haptics to disengage from the walls and engage portions of the eye itself. Once the lens is firmly held by the eye, the second member is also withdrawn.

BRIEF DESCRIPTION OF THE DRAWING

FIG. 1 shows a typical intraocular lens having haptics;

FIG. 2 is a plan view of the assembly;

FIG. 3 is a plan view of the first member;

FIG. 4 is a plan view of the second member;

FIG. 5 is a side view of the second member;

FIG. 6 is a side view of the first member;

FIG. 7 is an end view of the first member; and

FIG. 8 shows the tool being inserted into the capsular bag of an eye.

DESCRIPTION OF THE PREFERRED EMBODIMENT

A preferred embodiment of the invention shall now be described in relation to a posterior chamber lens. It must be understood however that the device would work equally well with an anterior chamber lens.

Referring to FIGS. 1–8, a typical intraocular lens 10 comprises a lenticular body 20 which is made out of a transparent material and has the required optical characteristics necessary to correct the patient's vision. A number of holes such as 30 are provided within the body to allow the surgeon to manipulate the lens. Imbedded in the body are two haptics or loops 40 and 50.

These loops are flexible, have a curvilinear shape in their relaxed or open position, and may be wrapped around the circumference of the body 20. This later position is referred to as the closed position.

The assembly comprises a first member 60 and a second member 70. Member 60 has a flat bottom 80 and two side walls 90 and 100. The side walls are oriented generally perpendicularly to bottom 80, but preferrably they lean towards each other, as shown in FIG. 7.

Member 70 has a bottom 75 with the general shape of bottom 80 and it is made to be introduced between walls 90 and 100 and slide on top of said bottom. At one end it has a raised lip 110. Member 70 also has a projection 120 whose purpose shall be clarified later. The two members are shown assembled in FIG. 2, with member 70 being disposed on top of bottom 80 between walls 90 and 100 of member 60. The two members cooperate to hold lens 10 as shown in FIG. 2. In effect, lens 10 is disposed on top of member 70 while its haptics 40 and 50 engage the walls 90 and 100 to hold the lens in place.

Prior to the insertion of the lens, an incision 150 is made in eye 160 between the cornea 170 and the choroidal tissues 180. The incision 150 need not be wider than the width of member 60. The end of the assembly which holds the lens is then inserted into the capsular bag until it reaches the desired position. During this step, the lens is resting against projection 120 and is stopped from shifting with respect to the assembly. Next, member 60 is withdrawn from the eye while the lens and the second member 70 are held in place by the surgeon who may use lip 110 for this purpose. Once member 60 is withdrawn, the haptics are free to expand within the bag and thus secure the lens to the eye. After the haptics have expanded, the second member 70 is also withdrawn from the eye.

One skilled in the art will appreciate the fact that during insertion, the haptics are held closed, and therefore, the risk of injuring the eye is reduced. The assembly also protects the capsular bag while the lens is being inserted. This facet of the invention becomes very important when the invention is used for an anterior chamber lens. As it was previously shown, the anterior chamber lens is installed above the iris, and above the ocular jelly contained in the anterior chamber. During any surgical operation, contact with this jelly must be avoided as much as possible. If the present invention is used to insert the lens, the jelly is protected by the assembly.

The assembly may be made of any of the common plastics in use today. Since it is very inexpensive to manufacture, it may be disposed after a single use, thus saving the sanitizing costs. Its size depends on the size of the lens. Preferrably member 60 should be about 15–18 mm long by 6–8 mm wide. Walls 90 and 100 may have a height of 1–1.5 mm. Second member 70 may be slightly shorter than member 60 or about 10–12 mm to allow member 60 to be pulled out of the eye first.

In summary, the present invention provides an inexpensive assembly for inserting an intraocular lens in an eye by keeping the haptics closed until after the lens has been positioned and without the use of awkward and bulky instruments. The assembly also protects the eye during the insertion procedure.

It will be apparent to those skilled in the art that various modifications of the invention may be made without departing from the scope of the invention as defined in the appended claims.

I claim:

1. An assembly for inserting an intraocular lens with haptics into an eye, comprising:
   a first member having a first member bottom with two sides and two opposing walls disposed along said sides structured and arranged to hold said lens therebetween; and
   a second member slidably disposed between said walls and having a second member bottom and a projection attached to said second member bottom for restricting the movement of a lens disposed in said assembly; said members being adapted to release said lens when said members are separated.

2. The assembly of claim 1 wherein said walls lean toward each other.

3. The assembly of claim 1 wherein said second member includes a lip provided as a holding means while the members are separated.

4. An assembly for inserting an intraocular lens into an incision of an eye comprising:
   a first member having a bottom of 6–8 mm wide by 15–18 mm long and two opposing walls having a height of 1–1.5 mm and provided to hold said lens therebetween;
   a second member slidably disposed between said walls and having a length of 10–12 mm; and
   said first and second member being adapted to release the lens held by said walls once the corresponding portion of the assembly is introduced into the incision by retracting said first member while said lens is held in place by said second member.

* * * * *